United States Patent [19]

Jain

[11] 4,276,140

[45] Jun. 30, 1981

[54] ELECTRODIALYSIS APPARATUS AND PROCESS FOR FRACTIONATING PROTEIN MIXTURES

[75] Inventor: Surendar M. Jain, Watertown, Mass.

[73] Assignee: Ionics Inc., Watertown, Mass.

[21] Appl. No.: 111,144

[22] Filed: Jan. 10, 1980

[51] Int. Cl.³ ............................................. B01D 57/02
[52] U.S. Cl. .................................. 204/180 P; 204/301
[58] Field of Search ............................. 204/180 P, 301

[56] References Cited

U.S. PATENT DOCUMENTS

| | | | |
|---|---|---|---|
| 3,829,370 | 8/1974 | Bourat | 204/180 P |
| 4,138,501 | 2/1979 | Chavéron et al. | 426/39 |
| 4,146,455 | 3/1979 | McRae | 204/180 P |

*Primary Examiner*—Aaron Weisstuch
*Attorney, Agent, or Firm*—Norman E. Saliba

[57] ABSTRACT

Apparatus and process for the fractionation of liquid solutions of protein mixtures which includes the steps of subjecting such solutions to electrodialysis (ED) while in the pH range of about between 5–8 until a partial or a substantially complete desalting takes place, the ED preferably being conducted between about 15° C. to 40° C., separating the fraction of protein which precipitates, passing the resulting supernatant salt depleted protein mixture into the concentrating compartments of the ED apparatus whereby the salts entering the salt concentrating chambers from the adjacent salt diluting chambers will substantially restore the original salt content of the desalted protein mixture.

8 Claims, 2 Drawing Figures

ELECTRODIALYSIS APPARATUS AND PROCESS FOR FRACTIONATING PROTEIN MIXTURES

FIELD OF THE INVENTION

This invention relates to the separation of complex protein mixtures by electrodialysis of the said mixtures to lower their ionic (salt) concentration, followed by chilling, filtration and/or pH adjustment, and thereafter restoring the lost electrolytes (ions) and water, especially during therapeutic plasma exchange that is performed in situ.

BACKGROUND OF THE INVENTION

Biological fluids like blood plasma or serum, milk, whey, urine, etc. contain a mixture of several proteins. For example, blood plasma contains albumin (3.5–4.5 g/100 ml), fibrinogen (0.20–0.45 g/100 ml), $\alpha$-globulins (0.4–1.0 g/100 ml), $\beta$-globulins (0.8 g/100 ml), immunoglobulin-IgG (0.8–1.8 g/100 ml), IgD (0.015 g/100 ml), IgA (0.09–0.45 g/100 ml), IgM (0.06–0.25 g/100 ml), etc. (Frank W. Putnam, The Trace Components of Plasma, An Overview). The immunoglobulins (Ig) are very important since they are involved in the proctective and defensive mechanism against infectious organisms. Clinical diseases characterized by imbalances of these systems of proteins, either in the ability to recognize invading mechanism or to recognize one's self, have promoted the basic understanding of the clinical aspects of the science of immunity. Abnormal immunological reactions are now known to cause a wide spectrum of diseases. Examples of diseases known to be associated with immune complex reactions include, for example, serum sickness, glomerulonephritis and myasthenia gravis. Plasmapheresis is a technique used to curtain, favorably interfere with or stop the immunopathologic process associated with circulating humoral antibody and/or immune complexes of the plasma. [Glassman, Rationale for Plasmapheresis, "Plasma Therepay", Vol. 1, Page 13 (1979)].

A known method is to plasmapherese about 4 liters of plasma over a period of 2–4 hours. The plasma removed from the patient is usually discarded and replaced by albumin and either physiological saline or Ringer's solution to make up the protein, electrolyte, and water balance. This is an expensive method and sometimes also leaves the patient in a hypoimmune state. In another method the make up of the removed plasma is accomplished by giving fresh frozen plasma, and though less expensive, suffers from the risk of transmitting hepatitis virus to the patient. The method of the present invention overcomes these problems by selectively removing euglobulins or euglobulin antigen complexes causing or resulting from the disease and at the same time restoring the major portions of albumin, electrolyte (salt) and water and thus returning to the patient his or her own plasma (without IgG-antigen) containing the proper protein, salt, and water balance. This technique makes the exchange less expensive and risk free from hepatitis since no additional albumin, salt, water or donor plasma is required. The present invention will be described using serum proteins as the principal example but the scope of this invention can also be applied to other biological fluids or other proteins without limiting the scope of the invention.

The present method thus generates a product capable of being used is situ without any additional modification of salt, protein or water content whereas the product of the prior art (Brown, U.S. Pat. No. 3,579,441) requires a make up of salts and water before any administration of the proteins back to the patient can be made and (Stern, 3,972,791) which requires cold (below 15° C.) processing and further purification steps.

THE INVENTION

The present invention relates to the application of electrodialysis to the fractionation or partial resolution of protein mixtures and restoration thereafter of their salt and water balance. The protein mixtures comprise principally (but not exclusively) plasma, serum or their derivative fractions. The electrodialysis process removes dissolved salts (ions) and consequently euglobulins or their complexes are substantially precipitated by a combination of ionic concentration, temperature and pH control. Albumin, and other proteins which are not euglobulin in nature, do not precipitate in a low salt solution and remain in solution for subsequent return to the patient. After removal of the euglobulin precipitates, the ionic concentration of the plasma is restored by using the salt depleted plasma as the salt receiving stream in the electrodialysis stack or module. The plasma can then be sent back to the patient without any further modification of the salt or water content.

More specifically, the invention comprises a process for fractionating liquid protein mixtures containing dissolved salt therein by employing an electrodialysis (ED) apparatus having one or more pairs of a salt concentrating and salt diluting chambers which are separated from each other by ion-selective membranes. A direct current is impressed across anode and cathode electrodes to reduce the salt content of the protein mixture located in the salt diluting chambers by transfering the salts from the diluting chambers to the adjacent salt concentration chambers. The desalted protein mixture from the diluting chambers is collected and treated to separate and remove therefrom one or more of the protein components. Thereafter the resulting salt depleted protein mixture is passed into the salt concentrating chambers whereby the salts entering the concentrating chambers from the adjacent diluting chambers will substantially restore to the desalted protein mixture its original salt and water content.

The process described above is especially adaptable where the liquid protein mixture is blood plasma or serum and where the protein components removed are euglobulins and/or their complexes.

An alternative manner of practicing the above described process is to collect the desalted protein mixture from the diluting chambers of the ED stack, remove one or more of the protein components from the desalted protein mixture and thereafter recycle the resulting salt depleted mixture back into the diluting chambers. The polarity of the direct current is then reversed so that the diluting chambers containing the salt depleted mixture now become salt concentrating or receiving chambers and the concentrating chambers containing the salts become diluting or salt depleting chambers. The salts transfered to the concentrating chambers thus substantially restore the original salt and water content of the desalted protein mixture.

DETAILED DESCRIPTION

Electrodialysis (ED) is widely practiced for desalting of aqueous solutions: brackish water, whey, milk (U.S. Pat. Nos. 3,433,726; 3,447,939; 3,595,766; 3,757,005;

3,754,650; etc.). These patents are concerned only with reducing the salt content of a liquid rather than using the ED process in a complex scheme of fractionating and balancing the salt and water content of a mixture of proteins including the therapeutic use as in cases of plasmapheresis.

Desalting by ion exchange column technology has been used in the past to cause precipitation and thus fractionate plasma proteins (U.S. Pat. Nos. 3,234,199; 3,073,744). This process however has limited flexibility and the columns are difficult to handle, clean and sterilize when employed under conditions necessary for protein fractionation.

It has now been discovered that electrodialysis can not only be used in the fractionation of proteins as a result of the desalting process but most importantly also to restore the electrolyte (salt) and water balance of the resulting desalted protein mixtures ready to be returned to the patient with substantially its original salts. The combination of techniques outlined herein include electrodialysis of the protein mixture, temperature and pH control, separation of certain proteins and thereafter restoration of the salt and water balance to the mixture. This novel method increases the usefulness of each step in a previously unexpected manner and makes the process extremely useful especially for in situ therapeutic use for plasmapheresis patients where removal of euglobulins or their complexes is required along with the restoration of the original plasma salt content. By this method, not only is the expense of albumin and salt replacement avoided but also the risk of contracting hepatitis inherent in the giving of fresh frozen plasma.

Figure 1:
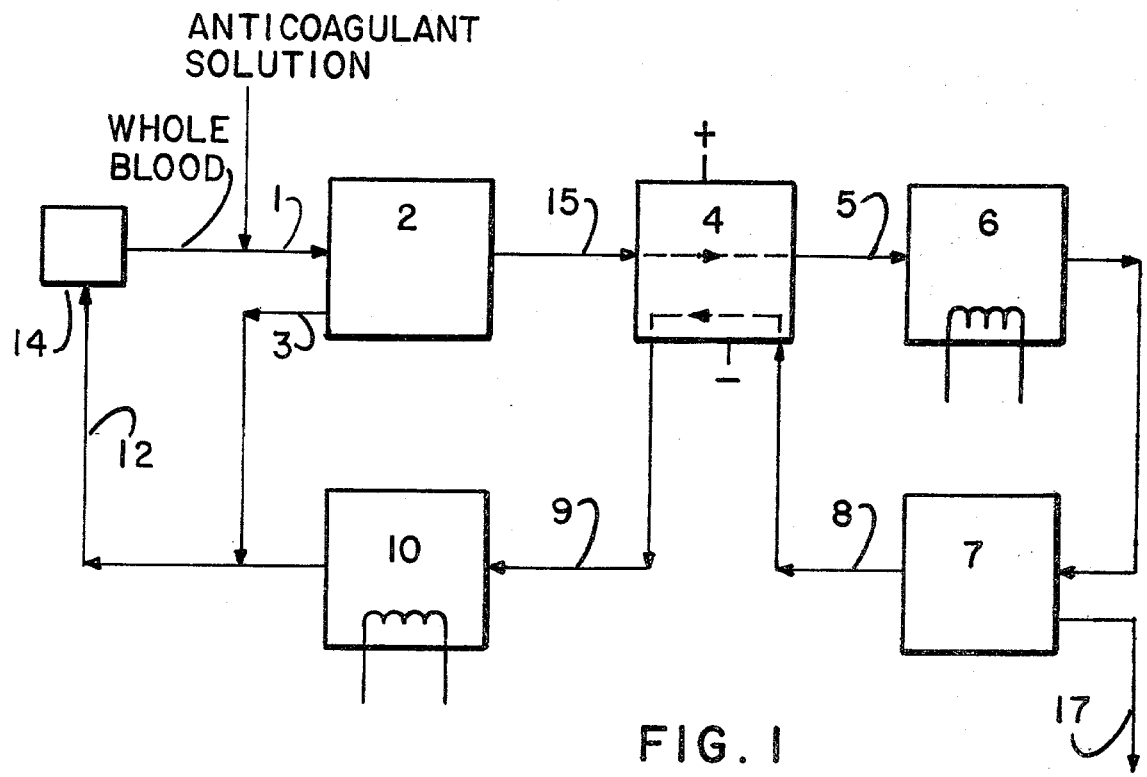

The process and apparatus will be hereinafter described by referring to FIGS. 1 and 2, where like parts are referenced with like numerals.

In the Figures the fluid under treatment is described with respect to plasma but it can be any other protein mixture. As shown in FIG. 1, citrated or heparinized blood 1 is ultrafiltered and/or centrifuged 2 to separate out the red cells 3, or any other suspension, and the remaining plasma 15 is sent to an electrodialysis (ED) stack 4 such as that which is manufactured by Ionics, Inc., Watertown, MA. Electrodialysis equipment and their methods of operation are more fully described in U.S. Pat. Nos. 2,848,403; 2,863,813; 3,003,940; 3,341,441; 4,115,225; and others. Such a stack normally comprises one or more pairs of concentrating and diluting chamber separated by alternating anion and cation exchange membranes. The chambers are located between an anode and a cathode. An electrolyte solution is preferably passed through the cathode and anode chambers to conduct current across the concentrating and the diluting chambers. Usually a concentrating chamber isolates the electrode solutions from the product or diluting chambers. The ion selective membranes are carefully selected so as to minimize any transfer of low molecular weight compounds such as blood sugars. The flow rates through the stack and the applied current is carefully regulated so that any excessive changes in pH are avoided. The plasma is passed into and through the diluting chambers and on impressing a direct current across the electrodes, the salt or ionic content of the plasma is reduced due to the passage of salt into the adjacent concentrating chambers which chambers may be primed initially with a small amount of plasma or albumin. The resulting desalted plasma 5 is collected from the diluting chambers (not shown) and passed into means for separating and removing one or more proteins (euglobulins or their complexes in this case). The separating means may, for example, consist of a heat exchanger 6 to lower temperatures, and centrifuging and/or ultrafiltration apparatus 7. After removal of the precipitated euglobulins 17 or other proteins, the salt depleted mixture 8 is passed into and through the concentrating chambers (not shown) of the ED stack thereby allowing it to receive the salts from the adjacent diluting chambers and hence restoring the original salt content of this desalted mixture. This salt restored mixture 9 is next passed through a heat exchanger 10 to adjust the mixture to body temperature where necessary, and then supplied with the red cells 3 previously separated from the plasma. This restored blood 12 can then be given back to the patient 14 without any outside addition of albumin or salts. Thus this process is self sufficient and capable of in-situ operation for therapeutic plasma exchange.

If the temperature of the plasma during electrodialysis is maintained in the range of about 15° to 40° C. and a current density (CD) to salt normality (N) ratio (CD/N) is kept in the range $$300-500 \; \frac{ma/cm^2}{eq/liter}$$

the precipitate so formed (even on complete desalting) is very fine thereby avoiding the potential problem of plugging the chambes of the ED stack.

Figure 2:
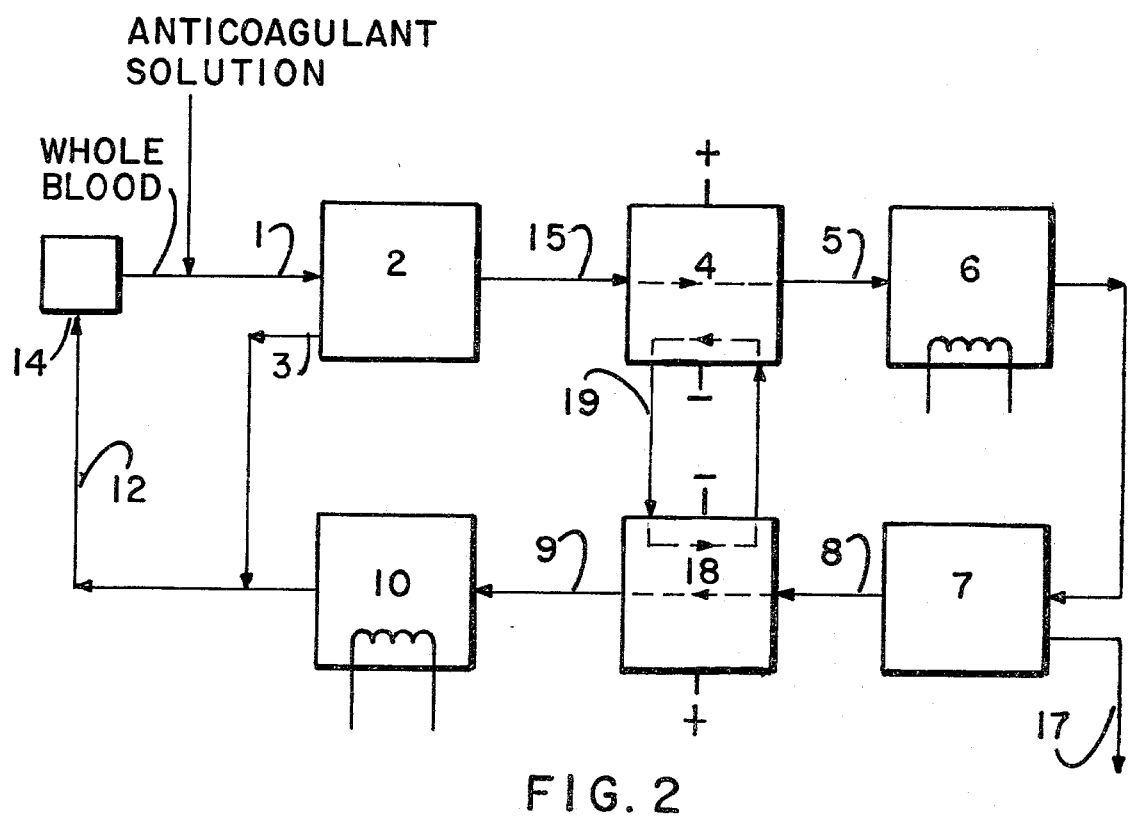

Another embodiment of the above apparatus and process is shown in FIG. 2. The fluid shown is again blood 1 but it can be any other protein mixture. The addition of citrate or heparin may or may not be needed and is added merely to keep the blood coagulation to a minimum during the processing. Again the heparinized or citrated blood is ultrafiltered or centrifuged 2 and then sent to an ED stack 4 similar to the one described in Example 1. The plasma is introduced into the diluting chambers and on passing a direct current across the stack the salts from the plasma are transferred to the concentrating chambers. The salt depleted mixture 5 from the diluting chambers is passed through a heat exchanger 6 to chill the plasma and the precipitate formed is separated 17 by an ultrafilter or a centrifuge 7. The desalted supernatant 8 is then fed to the diluting chamber of an electrodialysis stack 18. For the sake of clarifying this second operation another ED stack 18 is shown (in practice it can be the original ED stack 4) where the concentrating stream 19 of the ED stack 4 forms the other stream. The polarity for ED stack 18 is the reverse of ED-4 thus it causes the salts from the concentrate to go back to the desalted plasma thereby the salt balance is restored. This plasma 9 is then passed through a heat exchanger 10 and the red cells 3 are then combined with it and it can be given back to the patient 14. Thus this method offers another alternative to that described in FIG. 1.

EXAMPLE I

This example illustrates the restoration of the electrolyte and water balance of a desalted plasma using a fresh unsalted plasma in the dilute stream.

Apparatus used was a laboratory electrodialysis stack using only 1 cell pair (i.e. one diluting and one concentrating chamber). A 0.2N $Na_2SO_4$ solution was used for the electrode streams to conduct current. 360 ml of citrated unsalted plasma were used in the diluting stream and 340 ml of desalted plasma were used in the concentrating stream. The concentrating stream is the one that receives the salts. CD/N values used were $$400 \frac{ma/cm^2}{eq./liter}.$$

The progress of the run is summarized in the following table: The temperature was maintained at 15° to 20° C. in this run and the flow rates at 90 ml/min per cell pair. The effective cell pair area was about 220 cm$^2$.

| Time (min.) | Amps. | Dilute stream | | | Conc. stream (desalted phase) | | |
|---|---|---|---|---|---|---|---|
| | | Conductivity values | pH | vol. (ml) | Conductivity values | pH | vol. (ml) |
| 0 | 17 | 16,500 | 8.2 | 360 | 30 | 5.2 | 340 |
| 6 | 8.8 | 8,600 | 7.4 | 352 | 8,500 | 7.2 | 347 |
| 12 | 4.4 | 4,300 | 6.9 | 347 | 12,400 | 7.7 | 350 |
| 25 | 0.9 | 825 | 6.1 | 344 | 15,600 | 8.0 | 353 |
| 35 | 0.2 | 33 | 5.2 | 342 | 16,400 | 8.3 | 355 |

Thus the desalted plasma in the concentrating stream has been brought back to a conductivity value comparable to the original unsalted citrated plasma; the water balance has been restored. The conductivity values expressed above are in micromhos/cm.

EXAMPLE II

This example is similar to the above except that the desalted plasma is used in the dilute stream and the concentrating stream is a water solution containing the removed salts from a prior desalting run. The polarity of the current is reversed and the salts from the salt water stream are transferred to the desalted plasma to bring the salts of the plasma back to its original concentration.

The embodiments of this invention in which an exclusive property or privilege is claimed are defined as follows:

1. A process for fractionating liquid protein mixtures containing dissolved salts, by employing an electrodialysis apparatus having one or more pairs of concentrating and diluting chambers, the chambers being defined by alternating anion and cation exchange membranes located between terminally positioned anode and cathode electrodes, said process comprising passing the said protein mixture into the diluting chambers, impressing a direct current across said electrodes to reduce the salt content of said protein mixture by causing the passage of salt from the diluting chambers into the concentrating chambers, collecting the desalted protein mixture from said diluting chambers, separating and removing one or more protein components from the said desalted protein mixture and thereafter passing the resulting salt depleted mixture into said concentrating chambers whereby said salts entering said concentrating chambers from the adjacent diluting chambers will substantially restore the original salt content of said desalted protein mixture.

2. The process of claim 1 wherein the liquid the liquid protein mixture is selected from at least one of blood plasma and serum wherein the protein components removed are selected from globulins and euglobulins.

3. A process for fractionating liquid protein mixtures containing dissolved salts, by employing an electrodialysis apparatus having one or more pairs of concentrating and diluting chambers, the chambers being defined by alternating anion and cation exchange membranes located between terminally positioned anode and cathode electrodes, said process comprising passing the said protein mixture into the diluting chambers, impressing a direct current across said electrodes to reduce the salt content of said protein mixture by causing the passage of salt from the diluting chambers into the concentrating chambers, collecting the desalted protein mixture from said diluting chambers, separating and removing one or more protein components from the said desalted protein mixture, thereafter recycling the resulting salt depleted mixture back into said diluting chambers, and reversing the polarity of the direct current so that the said diluting chambers containing the salt depleted mixture now become salt concentrating chambers and the concentrating chambers containing salts become diluting chambers, whereby said salts will enter said concentrating chamber from the adjacent diluting chambers to substantially restore the original salt content of said desalted protein mixture.

4. The process of claim 3 wherein the liquid protein mixture is selected from at least one of blood plasma and serum and wherein the protein components removed are selected from globulins and euglobulins.

5. The process of claims 1 or 3 wherein the liquid protein mixture is whole blood that has been treated with anticoagulants followed by separation of the suspended blood cells prior to desalting.

6. An apparatus for fractionating liquid protein mixtures containing dissolved salts, comprising in combination an electrodialysis apparatus having one or more pairs of concentrating and diluting chambers, the chambers being defined by alternating anion and cation exchange membranes located between terminally positioned anode and cathode electrodes, means for passing the said protein mixture into the diluting chambers, means for impressing a direct current across said electrodes thereby reducing the salt content of said protein mixture by causing the passage of salt from the diluting chambers into the concentrating chambers, means for collecting the desalted protein mixture from said diluting chambers, means for separating and removing one or more protein components from the said desalted protein mixture and conduit means for passing the resulting salt depleted mixture into said concentrating chambers whereby said salts entering said concentrating the chamber from the adjacent diluting chambers will substantially restore the original salt content of said desalted protein mixture.

7. An apparatus for fractionating liquid protein mixtures containing dissolved salts, comprising in combination an electrodialysis apparatus having one or more pairs of concentrating and diluting chambers, the chambers being defined by alternating anion and cation exchange membranes located between terminally positioned anode and cathode electrodes, means for passing the said protein mixture into the diluting chambers, means for impressing a direct current across said electrodes thereby reducing the salt content of said protein mixture by causing the passage of salt from the diluting chambers into the concentrating chambers, means for collecting the desalted protein mixture from said diluting chambers, means for separating and removing one or more protein components from the said desalted protein mixture, conduit means for recycling the resulting salt depleted mixture back into said diluting chambers, and means for reversing the polarity of the direct current so that said diluting chambers containing the salt depleted mixture now become salt concentrating chambers and said concentrating chambers containing salts now become diluting chambers, whereby said salts will enter said concentrating chambers from the adjacent diluting chambers to substantially restore the original salt content of said desalted protein mixture.

8. The apparatus of claims 5 or 7, the liquid protein mixture is whole blood and wherein means for anticoagulating and thereafter separating the suspended blood cells are provided prior to passing the said protein mixture into the diluting chamber.

* * * * *